United States Patent [19]

Sasse

[11] 4,048,985
[45] Sept. 20, 1977

[54] EXERCISE DEVICE

[75] Inventor: Howard A. Sasse, Buffalo, N.Y.

[73] Assignee: H. Sass-E International Inc., Buffalo, N.Y.

[21] Appl. No.: 688,936

[22] Filed: May 21, 1976

[51] Int. Cl.² ............... A61B 5/00; A61H 19/00
[52] U.S. Cl. ............................ 128/2 S; 128/79
[58] Field of Search ........... 128/2 S, 79, 64, 360, 128/252, 344; 272/93, 68

[56] References Cited

U.S. PATENT DOCUMENTS

| 1,879,305 | 9/1932 | Kennedy | 128/344 |
| 2,541,520 | 2/1951 | Kegel | 128/2 S |
| 2,708,421 | 5/1955 | Jauch | 128/252 |
| 3,598,106 | 8/1971 | Buning | 128/2 S |

Primary Examiner—Lawrence W. Trapp

[57] ABSTRACT

The present invention relates to an exercise device. The device has a multiplicity of uses. It may be used to test or to strengthen muscles. It may be used to enable the user to develop or improve sexual skills. The device consists of an elongated flexible tube member connected in a fluid-tight manner to a pressure indicating means. Pressure exerted on the tube member is reflected on the pressure indicating means.

9 Claims, 2 Drawing Figures

FIG. 1

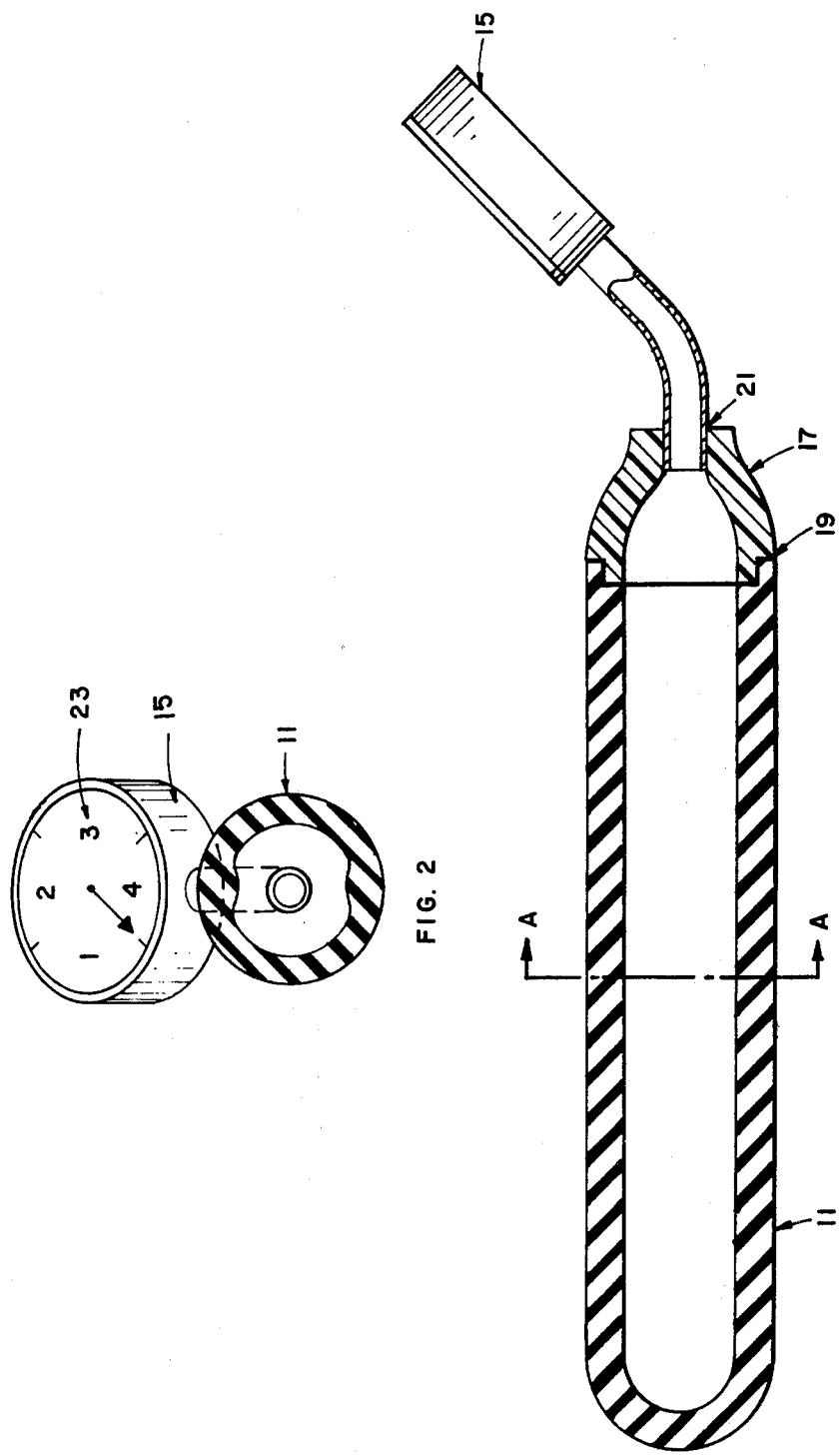

EXERCISE DEVICE

BACKGROUND OF INVENTION

Various devices have been utilized to aid in sexual encounters, e.g. dildoes, ticklers and the like. Such devices are utilized directly in the sexual activity. Although the device of the present invention can be utilized as a dildoe, the main purpose and use is to aid in strengthening muscles utilized in sexual encounters and not be used directly. The present device allows the user to develope skills in applying varying amounts of pressure at various times during sexual encounters so as to enhance the enjoyment of both partners. The device may be scaled to develop suitable hand pressure skills, but it is best adapted to test and develop muscles in the vagina. The device may be utilized to develop pressure skills in complete privacy. Such practice on a periodic routine basis with the device of the present invention can give the user knowledge and skill and applying such pressures in both amounts and time as to give maximum enjoyment to both sexual partners when such developed skills are used in actual sexual encounters.

SUMMARY OF INVENTION

The present invention relates to a device useful to strengthen and develop muscles and for aiding in measuring and controlling the force exerted. The present invention is useful in measuring and controlling the strength of the muscles of the human hand and body. The device includes an elongated tube equipped with a pressure indicating means whereby the user may determine the squeeze pressure along various portions of the tube as squeezing muscles are moved along various portions of the tube. Although useful in hand pressure development wherein the hand pressure may be varied by the user along the length of the tube, the invention is particularly adapted to use by women in strengthening and controlling internal muscles utilized in sexual congress.

The present invention consists of a flexible elongated tube having one rounded enclosed end. The tube has substantially circular cross-section. The end of the tube opposite the enclosed end is connected to a pressure indicating device, suitably a gauge, forming a fluid containing, closed system. When pressure is exerted on the outside of the tube, the force is indicated on the pressure indicating means. Suitably the pressure indicating means is positioned at an angle to the tube member to enable the user to easily view the scale and determine the pressure being applied. The tube member simulates a tumescent penis. In one mode of the invention the tube member is reinforced along its length by a plurality of elongated internal rib members, suitably at least two. The rib members give lengthwise rigidity to the flexible tube which is particularly desirable when the device is in use. The rib members are aptly formed by increasing the tube wall thickness along the length of the tube. The rib members may be separate strips lengthwise attached to the interior of the tube or may be in the form of a unit such as a cage which is inserted into the flexible tube. Suitably the rib members are positioned in pairs with the pair members being positioned substantially opposite each other inside the tube. Suitably the width of the rib members is from about 1/16 to about ¼ of the internal diameter of the tube and have a spacing apart of at least the width of a rib member.

The flexible tube member may be fabricated flexible material, such as, rubber or plastic. A latex rubber composition has been found well adapted. The tube member should be of a material to withstand washing with soaps and detergents and may be adapted with a collar or other connecting means to the pressure indicating means.

The form of the pressure indicating means is not critical to the present invention. Suitably it is a simple gauge with a broad scale read-out that may be color coded or with a minimal of numeric or alphabetic designations.

The closed, fluid tight, system formed by the tube member and the pressure indicating means may be filled with any fluid that will transmit pressure changes to the pressure indicating means. Thus the tube may contain a liquid or be partly filled with a liquid. Most practical, and particularly adapted to use in the closed system, is a gas, such as air.

The tube member may be suitably marked along its side to give the user index points to better judge the depth of insertion and the areas to be squeezed and to practice repeated movement of pressure from one area to another. Such marking may suitably be by rings around the tube member or by color coding. In one form the tube member has an outer surface which varies in a stepwise manner in diameter along the length of the tube member enabling the user to determine the depth of insertion by feel alone. In this embodiment two steps are usually found to be adequate.

BRIEF DESCRIPTION OF THE DRAWINGS

In the drawings,

FIG. 1 is a horizontal cross-section view of a typical device of the present invention.

FIG. 2 is a sectional view taken along lines A—A' of FIG. 1.

Looking now at the drawings in more detail, elongated tube 11 is fabricated of a flexible material, preferably of rubber or plastic. Although the outside surface of tube 11 may be serrated, it is preferable that it be smooth for best simulation and also ease in washing. Tube 11 is substantially cylindrical in cross-section and has closed end 13 which is suitably rounded to facilitate simulation and insertion into body orifices. Tube 11 is joined to a pressure indicating means, gauge 15 in a fluid tight manner. The joint may be made direct or may be made through an intervening component such as housing 17. One advantage of utilizing an intervening component is a commercially available gauge may be utilized as the pressure indicating means and needs only to be secured to the housing which is adapted to fit both tube 11 and gauge 15. Joints 19 and 21 are fluid tight so that pressure on any point of tube 11 and particularly along the side of tube 11 is reflected by the pressure measuring means, i.e. gauge 15 by reading on scale 23. As better shown in FIG. 2, tube 11 is preferably internally supported by rib members 25 along the length of tube 11 to better simulate a tumescent penis. Rib members 25 are easiest formed by an increased thickness in the side wall of tube 11 along the length of tube 11. The reinforcing or rib members may be independent of tube 11 and may be formed of strips or a cage member positioned within tube 11. The reinforcing means within tube 11 may be varied to suit the use or user. The pressure indicating means may also be adjusted to suit the use or user and scale 23 may be adapted to indicate pressure in a numerical, alphabetic or color code scale. Suitably gauge 15 is positioned at an angle from tube 11 to facilitate easier reading of the scale 23 when the device is in use.

In using the device externally, tube 11 may be squeezed by various parts of the body, for example hand, feet or breasts and readings on gauge 15 noted. Scale 23 broadly adapted to read in pressure categories of, for example, little feel, much feel, or pain. In internal use tube 11 is inserted, for example, in the vagina, and readings on scale 23 noted. Records may be maintained of readings to record increases of strength or to gain knowledge of the amount of strength that the user desires to employ is subsequent sexual intercourse. In a preferred use the device is employed each day on a routine basis so that the user can foretell which muscles can best be utilized and the most apt time of use when insertions other than the device are made in the user, e.g. during sexual intercourse.

What is claimed is:
1. An exercise device comprising in a single unit
   a. an elongated tube member simulating a tumescent penis,
   b. said tube member having a substantially circular outer cross-section, and having one rounded and enclosed and one open end,
   c. a pressure indicating means positioned contiguous to, and in fluid tight relation to said open end of said tube member, forming a closed gas-containing system,
   d. said pressure indicating means reflecting changes in pressure of said closed system.
2. The device of claim 1 where the tube member has a plurality of elongated rib members internally positioned within said tube.
3. The device of claim 2 wherein the rib members are formed by increased thickness in the side wall of said tube member.
4. The device of claim 1 wherein the pressure indicating means includes a scale.
5. The device of claim 1 wherein the pressure indicating means is positioned at an angle from the said tube member.
6. The device of claim 1 wherein the pressure indicating means is connected and in a sealed relation, to a housing member, and said housing member is connected and in a sealed relation, to said tube member.
7. The device of claim 1 wherein the gas is air.
8. The device of claim 1 wherein the tube member is fabricated of rubber.
9. The device of claim 1 wherein the side of said tube member is marked to indicate areas for pressure to be applied.

* * * * *